United States Patent [19]

Urbin

[11] 4,094,429

[45] June 13, 1978

[54] STOPPER FOR TEST TUBE, AND THE LIKE

[76] Inventor: Matthew C. Urbin, 4524 La Barca Dr., Tarzana, Calif. 91364

[21] Appl. No.: 708,402

[22] Filed: Jul. 26, 1976

[51] Int. Cl.² .......................................... B65D 41/00
[52] U.S. Cl. .................................. 215/305; 215/320; 215/354
[58] Field of Search ............... 215/320, 354, 305, 296, 215/299; 23/292

[56] References Cited

U.S. PATENT DOCUMENTS

| 2,168,734 | 8/1939 | Freeman | 215/320 |
| 2,372,182 | 3/1945 | Bar | 215/320 |
| 3,241,663 | 3/1966 | Kaepernik | 215/320 |
| 3,244,308 | 4/1966 | Esposito, Jr. | 215/354 |
| 3,380,610 | 4/1968 | Krieps | 215/320 |

FOREIGN PATENT DOCUMENTS

| 1,255,886 | 1/1961 | France | 215/320 |
| 471,834 | 9/1937 | United Kingdom | 215/320 |

*Primary Examiner*—Ro E. Hart
*Attorney, Agent, or Firm*—Keith D. Beecher

[57] ABSTRACT

A stopper is provided for a test tube, and the like, which can be quickly inserted into the mouth of the test tube into sealing engagement therewith by a simple pushing operation, and which can be just as quickly removed by a simple pulling operation. The stopper has a hat-like configuration. It is formed of rubber, or equivalent resilient material. The stopper is placed over the mouth of the test tube and is pushed inwardly until it assumes an inside-out configuration in which the stopper is firmly sealed to the mouth of the test tube. To remove the stopper, it is merely necessary to pull it back to its original configuration.

4 Claims, 3 Drawing Figures

STOPPER FOR TEST TUBE, AND THE LIKE

BACKGROUND OF THE INVENTION

In normal clinical and hospital procedures, test samples and specimens are taken from the patients, and these test samples and specimens are usually placed in test tubes, or similar containers. The test tubes are then labelled and sealed, and sent to the laboratory. At the laboratory, the test tubes must be repeatedly opened and closed as the specimens and samples are removed for each of a variety of tests. This opening and closing of the test tubes is a time-consuming operation, especially in the larger laboratories where thousands of specimens and samples are tested daily. The stopper of the present invention is advantageous in such situations since it can be placed in sealing relationship with a test tube by a simple pushing operation, and can subsequently be removed by a simple pulling operation.

Although the stopper of the invention will be described herein in conjunction with a test tube, it will become apparent as the description proceeds, that the stopper can be used in conjunction with a wide variety of bottles, and other receptacles, in which a removable stopper is required, which can easily be inserted into the mouth of the receptacle in a sealing relationship therewith, and just as easily removed.

DETAILED DESCRIPTION OF THE ILLUSTRATED EMBODIMENTS

Figure 2:
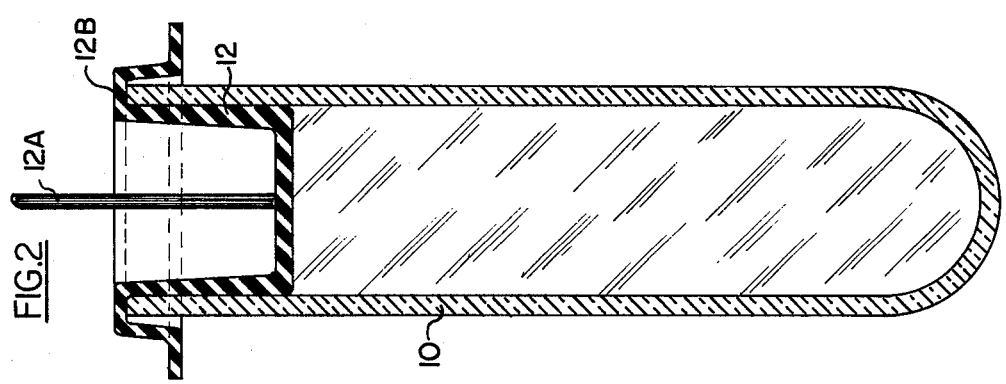
FIG. 2 is a view like FIG. 1, and showing the stopper pressed down to its closed, sealing position with respect to the mouth of the test tube.
Figure 1:
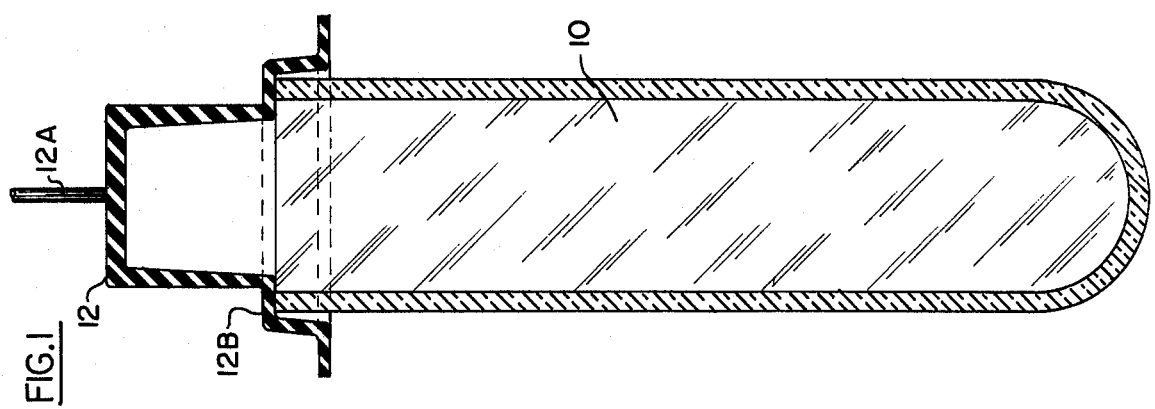
FIG. 1 is a side section of a stopper constructed in accordance with one embodiment of the invention is position over the mouth of the test tube before being pressed down to its closed, sealing position.

In the representation of FIGS. 1 and 2, a test tube 10 is provided, having an open mouth adapted to be sealed by a stopper 12, the stopper being constructed in accordance with one embodiment of the invention.

As shown in FIGS. 1 and 2, the stopper 12 has a hat-like configuration, and a generally rectangular longitudinal section. A rigid rod-like member 12A is attached to, or formed integral with the outer surface of the closed end of the stopper 12, and the member 12A extends outwardly from the closed end to constitute an operating handle.

The stopper 12 has a rim 12B surrounding its open end, and which is dimensioned to engage the upper edge surrounding the mouth of the test tube 10. The rim 12B is rigid, as is the closed end of the stopper. The side wall of the stopper is tapered to a thinner dimension adjacent to the rim 12, so as to form effectively a hinge for the stopper.

To close the end of the test tube 10, the stopper 12 is first placed on the open mouth of the test tube, as shown in FIG. 1. Then the stopper is pushed inwardly into the mouth of the test tube by the handle 12A, until it assumes an inside-out configuration, such as shown in FIG. 2. In the latter configuration, the stopper firmly engages the inner surface of the wall of the test tube adjacent to its mouth in a closed, sealing engagement therewith.

It will be appreciated that the stopper may be removed at any time, merely by pulling the handle 12A to restore the stopper to the configuration of FIG. 1. The stopper may just as easily be replaced on the test tube, merely by pushing the handle 12A inwardly into the mouth of the test tube, until the stopper assumes the configuration of FIG. 2.

Figure 3:
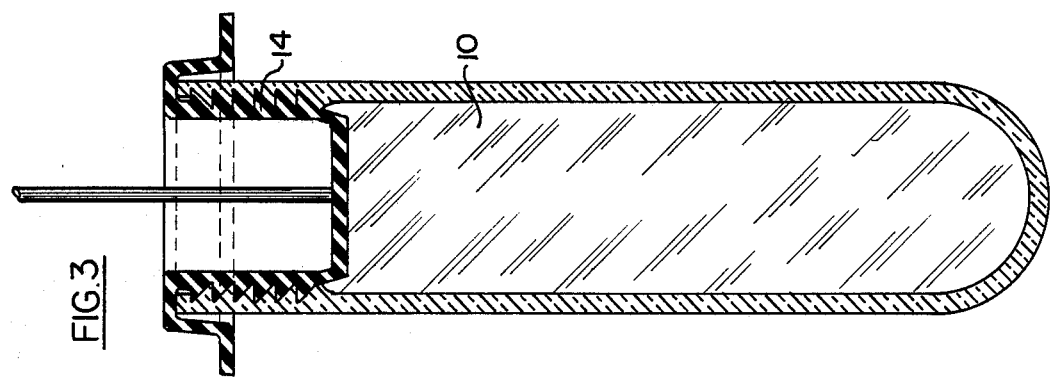
FIG. 3 is a view, like FIG. 2, of a second embodiment of the invention.

The stopper 14 in FIG. 3 is generally similar to the stopper 12, except that the inner surface of the stopper has a sawtooth configuration, so that when the stopper is pushed into the mouth of test tube 10, to assume its inside-out configuration the sawtooth surface of the stopper faces outwardly, and is received in a mating sawtooth surface in the wall of the test tube adjacent to its mouth, so as to enhance the sealing capabilities of the stopper.

While particular embodiments of the invention have been shown and described, modifications may be made. It is intended in the claims to cover the modifications which come within the true spirit and scope of the invention.

What is claimed is:

1. A stopper for sealing the mouth of a test tube, and the like, said stopper being formed of a resilient material, and having a hat-shape with a closed outer end and an open inter end, and having a peripheral rim surrounding said open inter end and dimensioned to engage the edge surrounding the mouth of the test tube in which the wall of the stopper tapers from a thicker to a thiner dimension from the closed end of the stopper to said peripheral rim and with the central portion of the stopper being adapted to be pushed inwardly into the mouth of the test tube to assume an inside-out configuration in sealing relationship with the inner wall of the test tube adjacent to the aforesaid edge.

2. The stopper defined in claim 1, in which the stopper has a generally rectangular longitudinal section.

3. The stopper defined in claim 1, in which the outer end and rim of the stopper are rigid, and the portion of the wall adjacent to the rim is resilient.

4. The stopper defined in claim 1, and which includes an elongated, rod-like member attached to said closed outer end and extending outwardly therefrom.

* * * * *